United States Patent [19]
Ganguly et al.

[11] 4,373,095
[45] Feb. 8, 1983

[54] MACROLIDE ANTIBACTERIAL AR-5 COMPONENTS

[75] Inventors: Ashit K. Ganguly, Upper Montclair; Olga Sarre, Verona; Yi-Tsung Liu, Parsippany, all of N.J.

[73] Assignee: Schering Corporation, Kenilworth, N.J.

[21] Appl. No.: 244,541

[22] Filed: Mar. 17, 1981

Related U.S. Application Data

[63] Continuation-in-part of Ser. No. 106,184, Dec. 21, 1979, abandoned.

[51] Int. Cl.$^3$ ............................................. C07H 17/06
[52] U.S. Cl. ..................................... 536/7.1; 424/180
[58] Field of Search ............................ 536/17 R, 17 C

[56] References Cited

U.S. PATENT DOCUMENTS

| 3,769,273 | 10/1973 | Massey | 536/17 R |
| 3,975,372 | 8/1976 | Ganguly et al. | 536/17 R |
| 4,056,616 | 11/1977 | Reimann et al. | 536/17 R |
| 4,279,896 | 7/1981 | Ganguly et al. | 536/17 R |
| 4,307,085 | 12/1981 | Waitz et al. | 536/17 R |

Primary Examiner—Johnnie R. Brown
Attorney, Agent, or Firm—Carver C. Joyner; Gerald S. Rosen; Gerald F. Swiss

[57] ABSTRACT

Desmycinosyl derivatives of 12,13-desepoxy-12,13-dehydro antibiotic AR-5 component 1 and 12,13-desepoxy-12,13-dehydro antibiotic AR-5 component 2 are useful antibacterial agents and may be converted to other such agents by processes analogous to those generally known in the art.

22 Claims, No Drawings

MACROLIDE ANTIBACTERIAL AR-5 COMPONENTS

This application is a continuation-in-part of copending application Ser. No. 106,184, filed Dec. 21, 1979, and now abandoned.

This invention relates to a class of macrolide antibacterial agents derived from antibiotics 12,13-desepoxy-12,13-dehydro antibiotic AR-5 component 1 and 12,13-desepoxy-12,13-dehydro antibiotic AR-5 component 2. The preparation of these antibiotics is described in U.S. application Ser. No. 93,080, filed Nov. 9, 1979, and now U.S. Pat. No. 4,307,085. It is also noted that British Pat. No. 2,020,647A, published Nov. 21, 1979 appears to disclose the preparation of the same macrolide starting materials.

DESCRIPTION OF THE INVENTION

The compounds of this invention may be depicted by the following structural formula:

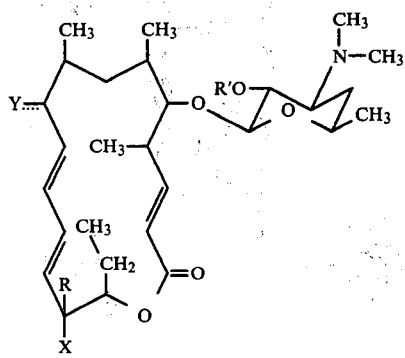

wherein R is a member of the group consisting of hydrogen and hydroxyl; R' is a member of the group consisting of hydrogen, and $C_2-C_{18}$ hydrocarbon carbonyl; Y is a member of the group consisting of oxo, hydroxyl and $C_2-C_{18}$ hydrocarbon carbonyloxy and the solid and dotted lines combined represent optionally a single or a double bond and X is a monovalent organic radical bonded by a carbon atom to the macrolide ring.

The compounds of this invention may be prepared by the treatment of 12,13-desepoxy-12,13-dehydro antibiotic AR-5 component 1 or 12,13-desepoxy-12,13-dehydro antibiotic AR-5 component 2 with dilute acid (0.5 N) at elevated temperatures (100° C.) which results in the cleavage of the glycosidically linked mycinose to yield a mixture consisting of an antibacterially active compound wherein the desosamine moiety is still attached to the aglycone and a free hydroxyl group occupies the position at C-21 formerly occupied by mycinose. Also produced is the bacterially inactive aglycone. The former compound is a key intermediate is that the hydroxyl group at the C-21 position may be converted to an aldehyde via treatment with the Jones or other oxidising reagent known in the art.

The addition to being convertible to an aldehyde moiety, the C-21 hydroxyl group has the further utility of being an antibacterial agent itself. Further, the C-21 hydroxy (desmycinosyl) derivatives may be induced to undergo glycoside formation with other sugars such as $\beta$-D-glucosyl, $\beta$-D-allosyl, 2-deoxy-$\beta$-D-glucosyl, 2-deoxy-62 -D-allosyl, 2,3-di-O-methyl-$\beta$-D-glucosyl, 2,3-di-O-methyl-$\beta$-D-allosyl, 2-deoxy-3-O-methyl-$\beta$-D-allosyl, 2-O-methyl-$\beta$-D-allosyl, 6-deoxy-$\beta$-D-alloxyl, 6-deoxy-2,3-di-O-methyl-$\beta$-D-gluoxyl, 2,6-dideoxy-3-O-methyl-$\beta$-D-allosyl, 6-deoxy-2-O-methyl-$\beta$-D-allosyl, $\beta$-D-galactonyl, 2,3-di-O-methyl-$\beta$-D-galactonyl, 2-O-methyl-$\beta$-D-galactonyl, 2-O-methyl-$\beta$-D-galactonyl, 6-deoxy-2,3-di-O-methyl-$\beta$-D-galactosyl, 6-deoxy-2-O-methyl-$\beta$-D-galactosyl, 2-O-methyl-$\beta$-D-galosyl, 6-deoxy-$\beta$-D-galosyl and 6-deoxy-2,3-di-O-methyl-$\beta$-D-galosyl. The foregoing glycosides of the C-21 hydroxy compounds are also useful antibacterial agents.

The glycosides of this invention may be prepared by the processes set forth in Angew. Chemical International Edition 1974, No. 3; pages 157–170 and the references cited therein.

As noted above, the starting materials for this invention are produced in the fermentation described in U.S. application Ser. No. 93,080, filed Nov. 9, 1979 and now U.S. Pat. No. 4,307,085, whose disclosure is hereby incorporated by reference herein. These starting materials (i.e. 12,13-desepoxy-12,13-dehydro antibiotic AR-5 component 1 and 12,13-desepoxy-12,13-dehydro antibiotic AR-5 component 2), may also be produced by chemical means from Antibiotic AR-5 component 1 and Antibiotic AR-5 component 2, respectively. For example, either Antibiotic AR-5 component 1 or Antibiotic AR-5 component 2 may be converted to the above described starting materials by reduction with chromous ions in a mineral acid solution in the same manner described in U.S. Pat. No. 3,975,372, issued Aug. 17, 1976 whose inventors include one of the inventors named herein. Thus, the four products disclosed in U.S. application Ser. No. 93,080 filed Nov. 9, 1979 and now U.S. Pat. No. 4,307,085, may be converted to the two starting materials utilized herein.

The C-21 hydroxyl being a primary alcohol is esterifiable by acylating agents known in the art. However, in view of the greater reactivity of the 2'-hydroxyl in the desosamine moiety, C-21 esters are prepared by indirect methods. For example, by treating the desmycinosyl derivative with an excess acylating agent such as acetic anhydride in a tertiary amine (pyridine), the 2',21-diacetate is formed. To obtain the 21-monoacetate, the 2',21-diacetate is subjected to selective solvolysis such as that described in U.S. Pat. No. 4,056,616 issued Nov. 1, 1977 whose disclosure is incorporated by reference herein. The inventors contemplate as being within the scope of this invention 2'-monoesters, 2',21-diesters and 21'-monoesters, the preparation of which is analogous to those disclosed in the referenced patent. In similar manner, the inventors contemplate as being within the scope of this invention the non-toxic pharmaceutically acceptable acid addition salts of the compounds of this invention. Suitable acids for preparing such salts are also set forth in the referenced patent.

The C-21 hydroxyl forms antibacterially active ethers by conventional means, however, in order to avoid competing reactions the 2'-position is esterified by treatment with an acylating agent in acetone. The 2'-ester is then treated with an alkyl, aryl or an aralkyl iodide and silver oxide. Whereby it is also possible to produce the corresponding quaternary salt of desosamine moiety. Alternatively, the ether derivatives may be prepared by treating the 2'-acyl C-21 hydroxyl derivative with sodium hydride and an alkyl, aryl or alralkyl halide in tetrahydrofuran. The 2'-hydroxyl function may be regenerated solvolysis using 80% methanol as described in the U.S. Pat. No. 4,056,616. In order to prepare ethers of alkyl, aryl or aralkyl compounds which bear hydroxyl and/or amino groups it is necessary to block the amino or hydroxyl function with blocking agents known in the art, perform the above described ether formation, then deblock the product.

The C-21 aldehydo derivative may be subjected to reductive amination procedures to form the corresponding C-21 amino group. For example, the C-21 aldehyde derivative upon treatment with a reducing agent such as sodium cyanoborohydride in combination with ammonium chloride is a facile method for producing the C-21 primary amine derivative. In the course of the reductive amination there is also produced the 9($\alpha,\beta$)dihydro derivative which may be converted back to the 9-keto function using reagents such as manganese dioxide, the Jones oxidation or similar oxidations known in the art.

The replacement of ammonium chloride with substituted (e.g. methyl) or disubstituted (e.g. dimethyl) aminating agents in the process affords the corresponding substituted or disubstituted C-21 amino derivatives from the C-21 aldehyde directly. The aminating agents are generally known in the art.

The terms substituted and disubstituted aminating agents is not limited to those used to prepare alkyl and dialkyl amino derivatives but also embraces those used to prepare amidines, guanidines, azetidines ureas and thiourea.

The C-21 primary amino derivatives may be procedures generally used in the art be converted to guanidines including cyclic guanidines, amidines, ureides or the like. Exemplification of these classical amino reactions which usually comprises an aminating portion and a leaving group such as halogen, an alkylthio, a dialkylamino, an alkoxy, a mesyloxy group or the like.

As is generally the case for any given class of compounds, some members of the class are preferred over others. The reasons for the preference may be due to ease of production, higher yields or better applied use characteristics. This invention is no exception. Thus, a preferred sub-class of this invention are compounds wherein the 9-ketone is reduced to a hydroxyl group i.e. the 9($\alpha, \beta$)-dihydro compounds. Another preferred sub-class of compounds are those wherein the subsituent at C-21 is a hydroxyl group. The 9($\alpha,\beta$)-dihydro compounds appear to exhibit an improved spectrum of activity than the parent compounds obtained from the fermentation. Thus the antibacterial compounds of this invention may be used to treat mammals having infections due to susceptible strains of such microorganisms.

The antibacterial agents of this invention may be used in the form of non-toxic pharmaceutically acceptable acid addition salts of mineral acids, organic acids including dibasic organic acids such as sulfates, phosphates, acetates, propionates, succinates, tartrates, citrates, maleates and the like. The compounds of this invention may also be used in the free form, in the form of non-toxic pharmaceutically acceptable esters and in the form of non-toxic acid addition salts of the esters.

The antibacterial compounds of this invention may be dispensed in the form of capsules, tablets, elixirs and as injectibles. Each of these dosage forms are to be prepared so as to permit the administration of from about 5 to about 50 mgs/kg per day in divided doses and may be administered in the same dosage forms set forth in U.S. application Ser. No. 93,080, filed Nov. 9, 1979 whose disclosure is incorporated by reference herein.

The Reaction Sequences set forth below are for exemplification and are not to be construed as limiting the scope of this invention.

R' and R''' independently are members of the group consisting of $C_1$–$C_8$ alkyl, $C_7$–$C_{18}$ aralkyl and $C_3$–$C_7$ heterocycle wherein the hetero atoms is sulfur, nitrogen or oxygen.

REACTION SEQUENCES

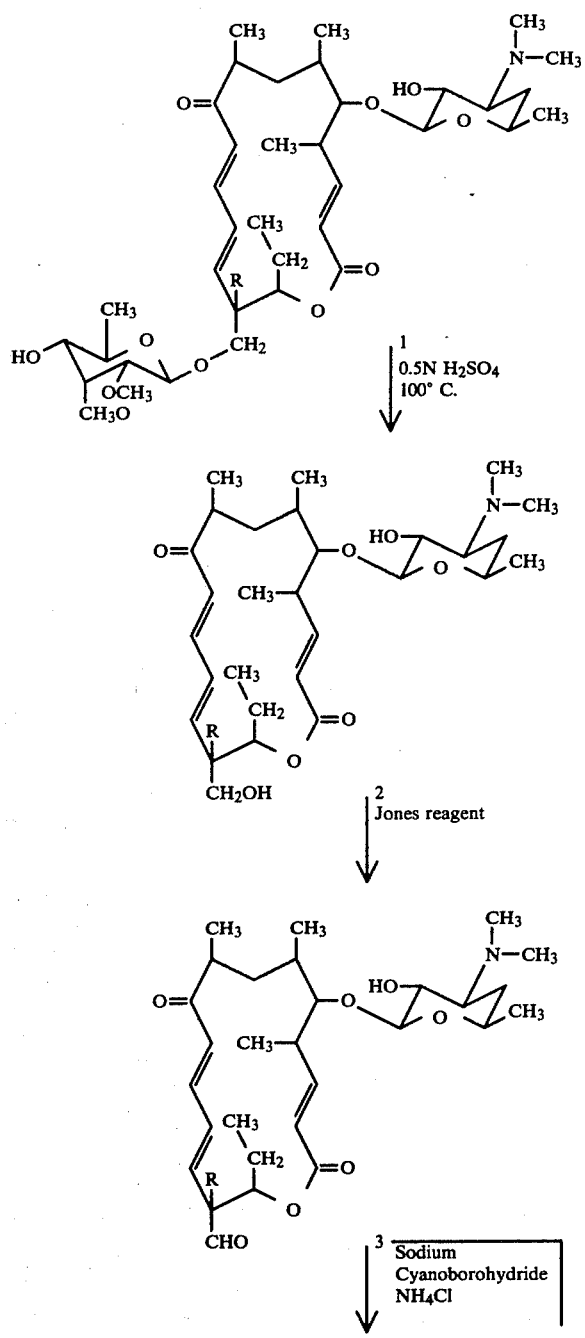

REACTION SEQUENCES
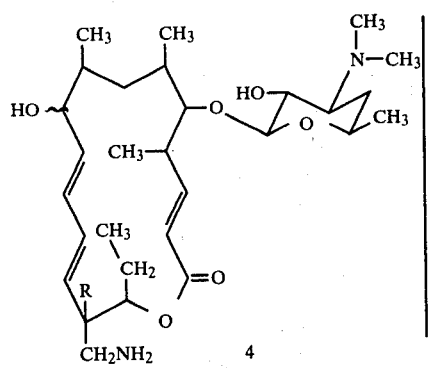
4
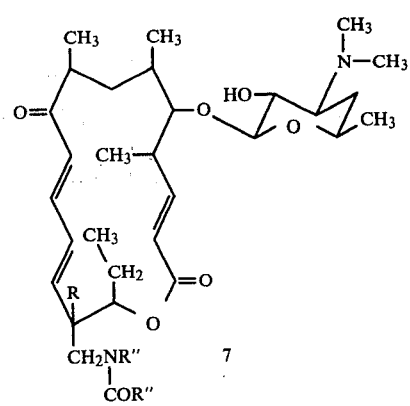
7
Wherein R and R″ are as previously defined.
R″NH₂
Sodium Cyanoborohydride
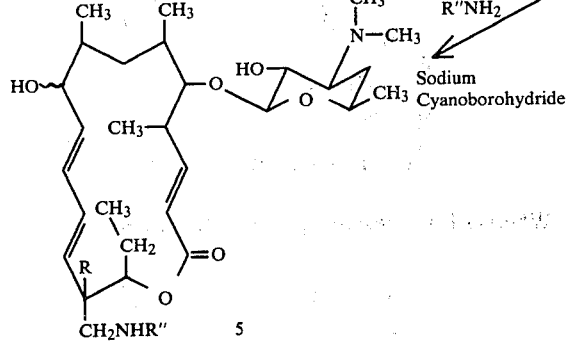
5
Wherein R and R″ are as previously defined.
Sodium Cyanoborohydride
HNR″R‴
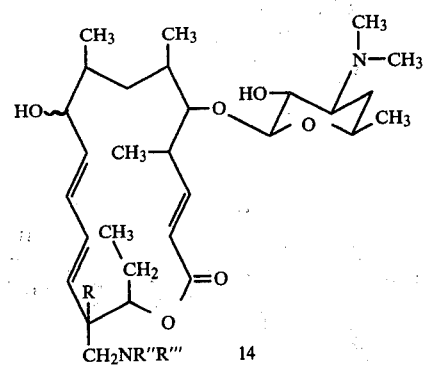
14
Wherein R, R″ are as previously defined and R‴ may be the same or different from R″ and is a member of the group defined for R″.
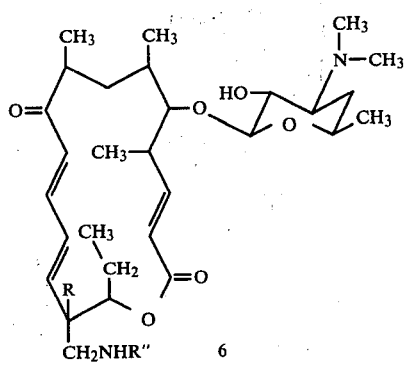
6
Wherein R and R″ are as previously defined.
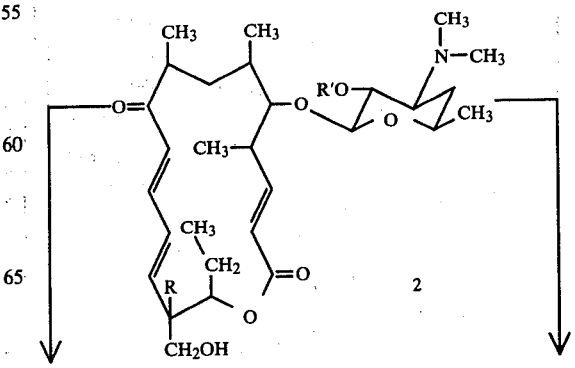
2
6 (R″CO)₂O

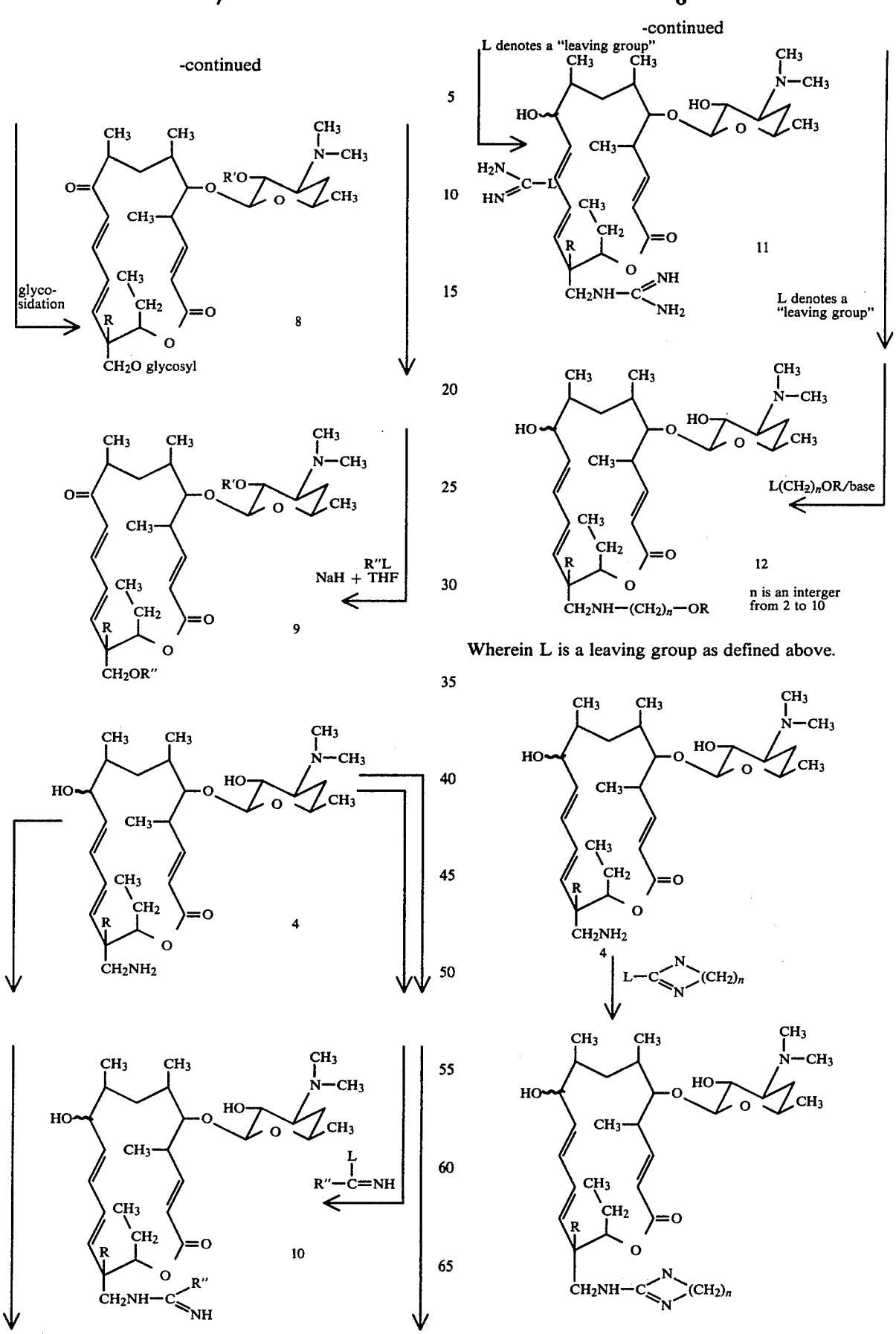
Wherein L is a leaving group as defined above.

n is an integer of from 2 to 6.

We claim:

1. A compound of the formula:

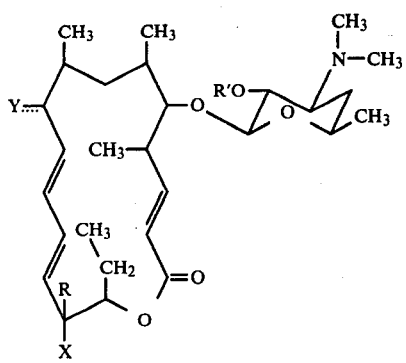

wherein R is a member of the group consisting of hydrogen and hydroxyl; R' is a member of the group consisting of hydrogen, and $C_2$-$C_{18}$ hydrocarbon carbonyl; Y is a member of the group consisting of oxo, and hydroxyl and solid and the dotted lines combined represent optionally a single or a double bond, and X is a monovalent organic radical bonded by a carbon atom to the macrolide ring, said X being a member selected from the group consisting of —$CH_2OR'$, —$CH_2OH$, —CHO, —$CH_2NH_2$, —$CH_2NHR''$, —$CH_2NR''R'''$, $CH_2OCOR''$, —$CH_2NHCOR''$ and —$CH_2O$-glycosyl, excluding mycinosyl and 3''-desmethylmycinosyl wherein R'' and R''' independently are members of the group consisting of $C_1$-$C_8$ alkyl, $C_7$-$C_{18}$ aralkyl and $C_3$-$C_7$ heterocycle wherein the hetero atom is sulfur, nitrogen or oxygen.

2. The compound of claim 1 wherein R and R' are hydrogen, Y is oxo and X is —$CH_2OH$, said compound being desmycinosyl 12,13-desepoxy 12,13-dehydro antibiotic AR-5 component 1.

3. The compound of claim 1 wherein R' is hydrogen, Y is oxo, R is hydroxyl and X is —$CH_2OH$, said compound being desmycinosyl 12,13-desepoxy 12,13-dehydro antibiotic AR-5 component 2.

4. The compound of claim 1 wherein R and R' are hydrogen, Y is hydroxyl and X is —$CH_2OH$, said compound being 9($\alpha,\beta$)-dihydro-desmycinosyl 12,13-desepoxy 12,13-dehydro antibiotic AR-5 component 1.

5. The compound of claim 1 wherein R is hydroxyl, R' is hydrogen, Y is hydroxyl and X is —$CH_2OH$, said compound being 9($\alpha,\beta$)-dihydro desmycinosyl 12,13-desepoxy 12,13-dehydro antibiotic AR-5 component 2.

6. A compound of claim 1 of the formula

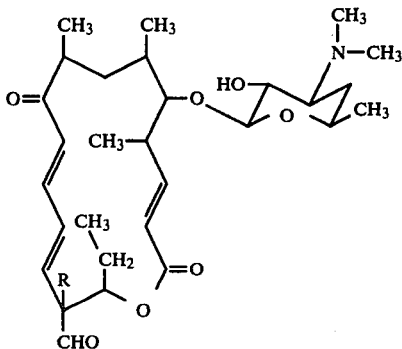

wherein R is as defined in said claim.

7. A compound of claim 6 wherein R is hydrogen.

8. A compound of claim 6 wherein R is hydroxyl.

9. A compound of claim 1 of the formula

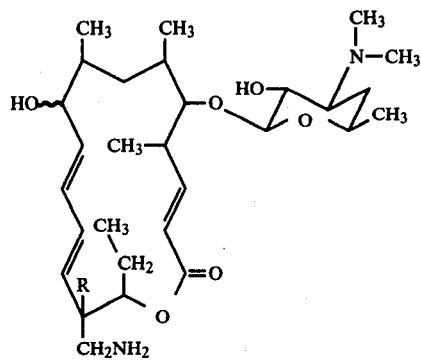

wherein R is as defined in said claim.

10. The compound of claim 9 wherein R is hydrogen, said compound being 9($\alpha,\beta$) dihydro-21-amino desmycinosyl-12,13-desepoxy 12,13-dehydro antibiotic AR-5 component 1.

11. The compound of claim 9 wherein R is hydroxyl, said compound being 9($\alpha,\beta$) dihydro-21-amino desmycinosyl-12,13-desepoxy 12,13-dehydro antibiotic AR-5 component 2.

12. A compound of claim 1 of the formula

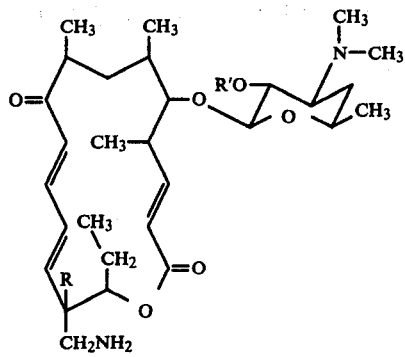

wherein R and R' are as defined in said claim.

13. A compound of claim 12 wherein R and R' are hydrogen, said compound being 21-amino desmycinosyl 12,13-desepoxy 12,13-dehydro antibiotic AR-5 component 1.

14. A compound of claim 12 wherein R is hydroxyl and R' is hydrogen, said compound being 21-amino desmycinosyl 12,13-desepoxy 12,13-dehydro antibiotic AR-5 component 2.

15. A compound of claim 1 of the formula

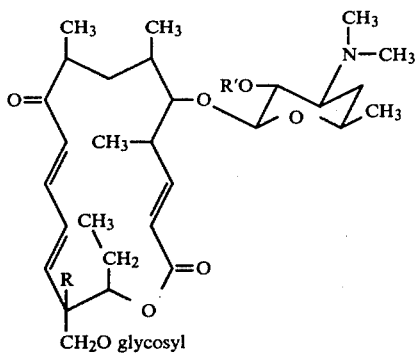

wherein R and R' are as defined in said claim and wherein the glycosyl group is other than mycinosyl and 3''-desmethylmycinosyl.

16. A compound of claim 1 of the formula

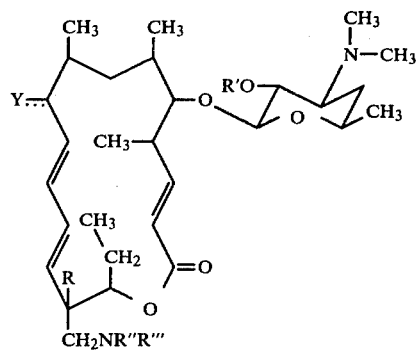

wherein R, R', R'', R''' and Y are as defined in said claim.

17. A compound of claim 16 wherein R and R' are hydrogen, R'' and R''' may be the same or different and are $C_1$–$C_{18}$ alkyl, and Y is as defined in said claim.

18. The compound of claim 17 wherein R'' and R''' are methyl and Y is oxo, said compound being 21-dimethylamino-desmycinosyl 12,13-desepoxy 12,13-dehydro antibiotic AR-5 component 1.

19. A compound of claim 16 wherein R is hydroxyl, R' is hydrogen, R'' and R''' may be the same or different and are $C_1$–$C_{18}$ alkyl and Y is as defined in said claim.

20. The compound of claim 19 wherein R'' and R''' are methyl and Y is oxo, said compound being 21-dimethylamino-desmycinosyl 12,13-desepoxy 12,13-dehydro antibiotic AR-5 component 2.

21. A compound of claim 16 wherein R and R' are hydrogen, R'' and R''' are combined to form a $C_3$–$C_7$ heterocycle wherein the hetero atom is nitrogen and Y is oxo.

22. The compound of claim 21 wherein R'' and R''' are combined to form a member of the group consisting of azetidino, amidino and guanidino.

* * * * *